(12) United States Patent
Jacobson et al.

(10) Patent No.: US 8,394,077 B2
(45) Date of Patent: Mar. 12, 2013

(54) CONTROLLED DELIVERY OF SUBSTANCES SYSTEM AND METHOD

(75) Inventors: Andrew D. Jacobson, San Antonio, TX (US); Jeff Sommers, Boerne, TX (US); Rasmus T. Kölln, Schweriu (DE); Kenneth R. Rose, San Antonio, TX (US)

(73) Assignee: Jacobson Technologies, LLC, San Antonio, TX (US)

( * ) Notice: Subject to any disclaimer, the term of this patent is extended or adjusted under 35 U.S.C. 154(b) by 130 days.

(21) Appl. No.: 12/796,874

(22) Filed: Jun. 9, 2010

(65) Prior Publication Data

US 2011/0087189 A1     Apr. 14, 2011

Related U.S. Application Data

(60) Provisional application No. 61/185,507, filed on Jun. 9, 2009.

(51) Int. Cl.
*A61M 31/00*     (2006.01)
(52) U.S. Cl. ........................................ 604/507; 604/151
(58) Field of Classification Search .............. 604/65–67, 604/131, 151, 246, 502–507, 533–284, 890.1–892.1
See application file for complete search history.

(56) References Cited

U.S. PATENT DOCUMENTS

| | | |
|---|---|---|
| 4,464,178 A | 8/1984 | Dalton |
| 4,687,468 A | 8/1987 | Gianturco |
| 4,781,695 A | 11/1988 | Dalton |
| 4,784,646 A | 11/1988 | Feingold |
| 4,857,053 A | 8/1989 | Dalton |
| 4,861,341 A | 8/1989 | Woodburn |
| 4,889,528 A | 12/1989 | Nadai et al. |
| 5,104,374 A | 4/1992 | Bishko et al. |
| 5,328,465 A | 7/1994 | Kratoska et al. |
| 5,609,572 A * | 3/1997 | Lang ............................... 604/22 |
| 5,637,088 A | 6/1997 | Wenner et al. |
| 5,792,056 A * | 8/1998 | Prince ........................... 600/420 |
| 5,813,972 A | 9/1998 | Nazarian et al. |
| 5,989,239 A | 11/1999 | Finch et al. |
| 6,007,516 A | 12/1999 | Burbank et al. |

(Continued)

FOREIGN PATENT DOCUMENTS

| | | |
|---|---|---|
| WO | 9956117 | 11/1999 |
| WO | 02036044 | 10/2002 |

(Continued)

OTHER PUBLICATIONS

USPTO Office Communication for U.S. Appl. No. 11/836,738 mailed Apr. 18, 2011.

(Continued)

*Primary Examiner* — Nicholas Lucchesi
*Assistant Examiner* — Gerald Landry, II
(74) *Attorney, Agent, or Firm* — Meyertons, Hood, Kivlin, Kowert & Goetzel, P.C.; Eric B. Meyertons (57) ABSTRACT

A fluid infusion system is described. Certain embodiments include an infusion syringe assessment device that assesses one or more characteristics of an infusion syringe coupled to a fluid infusion pump during use. The system may include a fluid infusion pump configured to accept the infusion syringe. The fluid infusion pump may advance an infusion fluid to a test subject in accordance with an infusion routine based on one or more of the assessed characteristics of the infusion syringe. The infusion routine may include at least one rate, at least one volume, at least one start time, at least one end time, and/or at least one duration.

26 Claims, 8 Drawing Sheets

U.S. PATENT DOCUMENTS

| | | | |
|---|---|---|---|
| 6,039,712 | A | 3/2000 | Fogarty et al. |
| 6,062,224 | A * | 5/2000 | Kissinger et al. ............ 128/897 |
| 6,293,922 | B1 | 9/2001 | Haase |
| 6,542,850 | B2 | 4/2003 | Ulman et al. |
| 6,544,214 | B1 | 4/2003 | Utterberg |
| 6,558,347 | B1 | 5/2003 | Jhuboo et al. |
| 6,595,756 | B2 | 7/2003 | Gray et al. |
| 6,616,630 | B1 | 9/2003 | Woehr et al. |
| 6,685,668 | B1 | 2/2004 | Cho et al. |
| 6,690,280 | B2 | 2/2004 | Citrenbaum et al. |
| 6,740,072 | B2 | 5/2004 | Starkweather et al. |
| 6,790,198 | B1 | 9/2004 | White et al. |
| 6,864,914 | B1 | 3/2005 | Birk |
| 6,940,403 | B2 | 9/2005 | Kail, IV |
| 6,998,980 | B2 | 2/2006 | Ingley, III et al. |
| 7,050,887 | B2 | 5/2006 | Alvarez |
| 7,056,307 | B2 | 6/2006 | Smith et al. |
| 7,056,316 | B1 | 6/2006 | Burbank et al. |
| 7,059,275 | B2 | 6/2006 | Laitinen et al. |
| 7,204,823 | B2 | 4/2007 | Estes et al. |
| 7,236,936 | B2 | 6/2007 | White et al. |
| 7,269,516 | B2 | 9/2007 | Brunner et al. |
| 7,300,418 | B2 | 11/2007 | Zaleski |
| 7,347,819 | B2 | 3/2008 | Lebel et al. |
| 7,347,854 | B2 | 3/2008 | Shelton et al. |
| 7,628,776 | B2 | 12/2009 | Gibson et al. |
| 2003/0050626 | A1 | 3/2003 | Gibson et al. |
| 2004/0054320 | A1* | 3/2004 | Kissinger et al. .......... 604/93.01 |
| 2004/0171983 | A1* | 9/2004 | Sparks et al. .................. 604/65 |
| 2007/0179436 | A1* | 8/2007 | Braig et al. ..................... 604/66 |
| 2008/0255500 | A1* | 10/2008 | Kissinger et al. .............. 604/28 |
| 2008/0306437 | A1 | 12/2008 | Jacobson et al. |
| 2009/0053086 | A1 | 2/2009 | Navarro |
| 2009/0196775 | A1 | 8/2009 | Navarro |
| 2009/0234275 | A1 | 9/2009 | Jacobson et al. |
| 2009/0234285 | A1 | 9/2009 | Jacobson et al. |
| 2009/0234286 | A1 | 9/2009 | Jacobson et al. |
| 2011/0087189 | A1 | 4/2011 | Jacobson et al. |

FOREIGN PATENT DOCUMENTS

| | | |
|---|---|---|
| WO | 2005079891 | 1/2005 |
| WO | 2010144533 | 12/2010 |

OTHER PUBLICATIONS

USPTO Office Communication for U.S. Appl. No. 11/836,738 mailed Jun. 15, 2011.

USPTO Office Communication for U.S. Appl. No. 12/107,470 mailed May 13, 2011.

Co-pending U.S. Appl. No. 12/107,470 entitled "Systems and Methods for Controlled Substance Delivery Network", to Jacobson et al., filed Apr. 22, 2008.

Co-pending U.S. Appl. No. 12/426,090 entitled "Controlled Substance Distribution Network Systems and Methods Thereof", to Jacobson et al., filed Apr. 17, 2009.

Co-pending U.S. Appl. No. 12/426,102 entitled "Systems and Methods for Controlled Substance Distribution Network", to Jacobson et al., filed Apr. 17, 2009.

Co-pending U.S. Appl. No. 12/426,086 entitled "Controlled Substance Distribution Network Systems and Methods Thereof", to Jacobson et al., filed Apr. 17, 2009.

Co-pending U.S. Appl. No. 12/796,874 entitled "Controlled Delivery of Substances System and Method", to Jacobson et al., filed Jun. 9, 2010.

Co-pending U.S. Appl. No. 11/836,738 entitled "Improved Medical Device with Septum", to Jacobson et al., filed Aug. 9, 2007.

"Instech Solomon" Apr. 2007. (pp. 1-57).

International Search Report and Written Opinion for PCT/US2010/037905, mailed Aug. 20, 2010. (pp. 1-15).

USPTO Office Communication for U.S. Appl. No. 12/426,090 mailed Jan. 7, 2011.

USPTO Office Communication for U.S. Appl. No. 12/426,102 mailed Jan. 7, 2011.

USPTO Office Communication for U.S. Appl. No. 11/836,738 mailed Oct. 13, 2010.

"PHM-111-EC Advanced Syringe Pump with Computer Control" http://www.med-associates.com/pumps/phm111.htm#111ec, web page update date: Aug. 15, 2008. (pp. 1-4).

"NE 1000 Family Detailed Features" web archive address: http://web.archive.org/web/20060209012340/http://www.syringepump.com/detailedfeatures.htm; web archive dated Feb. 9, 2006. (pp. 1-4).

* cited by examiner

$F = DV / (Tt - Ts)$ $F_{upperlimit} > F > F_{lowerlimit}$

F=flow (delivery) rate
DV=dead volume of tubing set
Tt=target time=scheduled time for the test article's leading edge to enter the animal's bloodstream
T=start time=time pump begins infusing (delivering) test article after a maintenance-to-test article syringe change
$F_{upperlimit}$ and $F_{lowerlimit}$ are values set by operator

---

$F = Tt - (DV / F)$ $F_{upperlimit} > F > F_{lowerlimit}$

F=flow (delivery) rate
DV=dead volume of tubing set
Tt=target time=scheduled time for the test article's leading edge to enter the animal's bloodstream
Ts=start time=time pump begins infusing (delivering) test article after a maintenance-to-test article syringe change
$F_{upperlimit}$ and $F_{lowerlimit}$ are values set by operator

FIG. 4

M=maintenance fluid
TA=test article fluid

FIG. 5D m=maintenance fluid
ta=test article fluid tubing set filled with Maintenance fluid tubing set filled with Maintenance fluid and with Test Article fluid tubing set filled with Maintenance fluid and attached to 10mL Maintenance syringe tubing set filled with Maintenance fluid and attached to 5mL Test Article syringe 10 mL assembled syringe 5 mL assembled syringe disassembled syringe

FIG. 6

Tubing set dead volume= 0.25 ml
Test article syringe size= 5 ml
Maintenance syringe size= 10 ml
Test article delivery rate= 2.5 ml/hr
Maintenance delivery rate= 0.25 ml/hr
Test article target value= 5 ml/day
M = Maintenance fluid
TA = Test Article fluid

| | Date | Time (1) (hh:mm) | Elapsed time (hh:mm) | Cume time (2) (hh:mm) | Pump status | Syringe type in pump | Animal status | Syringe size in pump (mL) | Delivery rate (mL/hour) | Cume TA vol (3): (mL) | Test Article syr. in pump? | Test Article in tubing set? |
|---|---|---|---|---|---|---|---|---|---|---|---|---|
| 1 | 16-May-06 | 9:00 | | | delivering M | M | receiving M | 10 | 0.25 | -- | no | no |
| 2 | 16-May-06 | 10:14 | | 0:00 | stop pump; switch syringes | switch to TA | stop | 5 | -- | -- | yes | no |
| 3 | 16-May-06 | 10:15 | | 0:03 | switch rate; start deliv of TA | TA | receiving M | 5 | 2.5 | -- | yes | yes |
| 4 | 16-May-06 | 10:18 | 0:03 | 0:06 | delivering TA | TA | receiving M | 5 | 2.5 | -- | yes | yes |
| 5 | 16-May-06 | 10:21 | 0:06 | | delivering TA | TA | receiving TA | 5 | 2.5 | 0.000 | yes | yes |
| 6 | 16-May-06 | 10:42 | 1:21 | | delivering TA | TA | receiving TA | 5 | 2.5 | 3.375 | yes | yes |
| 7 | 16-May-06 | 12:15 | 0:27 | 1:27 | stop pump; switch syringes | switch to M | stop | 10 | -- | 4.750 | no | yes |
| 8 | 16-May-06 | 12:16 | | 1:59 | Start Maint | M | receiving TA | 10 | 2.5 | 5.000 | no | yes |
| 9 | 16-May-06 | 12:22 | 0:06 | 2:00 | delivering Maint | M | receiving TA | 10 | 2.5 | 0.000 | no | yes |
| 10 | 16-May-06 | 12:22 | | | switch rate | M | receiving M | 10 | 0.25 | -- | no | no |
| 11 | 16-May-06 | 12:54 | 10:37 | | delivering Maint | M | receiving M | 10 | 0.25 | -- | no | no |
| 12 | 17-May-06 | 10:14 | 11:20 | | stop pump; switch syringes | switch to TA | stop | 5 | -- | -- | yes | no |
| 13 | 17-May-06 | 10:15 | | 0:00 | switch rate; start deliv of TA | TA | receiving M | 5 | 2.5 | 0.000 | yes | yes |

FIG. 7

NOTES:
(1) Time is rounded up to the nearest minutes
(2) Cumulative time from start of Test Article syringe delivery
(3) Cumulative volume of Test Article solution delivered to animal since change to Test Article syringe
(4) Test Article solution exiting the open end of the tubing set and entering the animals bloodstream

FIG. 8

CONTROLLED DELIVERY OF SUBSTANCES SYSTEM AND METHOD

PRIORITY CLAIM

This patent application claims priority to U.S. Provisional Patent No. 61/185,507 entitled "CONTROLLED DELIVERY OF SUBSTANCES SYSTEM AND METHOD" to Jacobson et al. filed on Jun. 9, 2009.

BACKGROUND

1. Field of the Invention

The present invention generally relates to a system and method for controlled delivery of substances and more particularly to controlled infusion of test substances to a test subject.

2. Description of Related Art

The pharmaceutical industry, contract research organizations, academia, and government entities routinely test the efficacy and safety of new chemical entities using intravenous infusion in laboratory animals such as, rats, dogs, and certain nonhuman primates. In some cases, large-scale toxicology infusion studies that can be used to assess the safety of new chemical entities are performed on a number of subjects. For instance, studies may assess several hundred animals for extended periods of time (e.g., many months or more). In other cases, drug metabolism, pharmacology, or safety pharmacology studies are performed using fewer animals over shorter periods.

These studies and other veterinary and/or human medical and research applications may include the use of medical and laboratory infusion pumps (e.g., electromechanical infusion pumps and other pumps). Infusion pumps may include, for instance, numerous types of electromechanical infusion pumps such as syringe, piston, peristaltic, diaphragm, large volume, stationary ("pole mount"), and portable ("ambulatory") type pumps. Other infusion pumps utilize gravity, springs, pneumatics, hydraulics, gases and other means. These pumps may be used to deliver a fluid (e.g., a new chemical entity) at a controlled delivery rate to a laboratory test animal, for instance. Similar pump technologies may be used for laboratory animal infusion and human-use infusion. Often, methods for human-use infusion (e.g., in a healthcare application) may be tailored to a single patient's needs while laboratory animal infusion (e.g., in an industrial or research application) may include common parameters tailored for use with multiple animals.

During studies, test substances may be delivered to a test subject, such as a laboratory animal, via a fluid delivery system conduit. For example, the test subject may be connected to an infusion pump (e.g., a syringe pump) using a network of components to carry the fluid from a pump fluid reservoir (e.g., a syringe) to the test subject. The network of fluid-carrying components, which may be referred to as "tubing set", may include various combinations of catheter, needle, cannula, polymeric tubing, fluid swivel, luer connectors, stopcocks, metal tubing for connecting polymer tubing, air filters, particle filters, etc. During use, the steps of loading, unloading, programming, starting and stopping one or more pumps, and adding or removing fluid delivery conduit systems are typically performed manually. For example, operators may manually enter one or more delivery rates into a pump, load a fluid-filled syringe into the pump, start fluid delivery from the pump by pressing a start button on the pump, and stop the pump by pressing a stop button. Further, users may manually document, using pen and paper or using a computer according to Good Laboratory Practices (GLP's), all these steps, as typically required by regulatory bodies, such as the Unites States Food and Drug Administration (FDA). The recorded data may include the type of fluid solution delivered by a pump, a user name, a time and date of each step, and description of the cause and/or resolution of pump alarms (e.g., occlusion alarms, syringe empty alarms, and other alarms indicating adverse pumping conditions). These steps may be complex, time consuming, labor intensive (e.g., requiring many operator man-hours), and increase the likelihood of human error. Additionally, these steps may provide undesirable contact between an operator and a test subject. For example, undesirable contact may occur in the case of containment (e.g., of allergens, disease, and other contamination), need for reduction of stimulation of test subject (e.g., the study of physiological parameters including heart rate and blood pressure), and other cases.

Accordingly, it may be desirable to provide a technique (e.g., system and/or method) that reduces the complexity of delivering test substances to a test subject. It may be desirable to provide techniques suitable for automating certain aspects of the toxicologic infusion study processes. Automating certain aspects of the processes may reduce the man-hours required for infusion studies, improve the quality of infusion studies by reducing the likelihood of human error, and/or reduce operator contact with test subjects.

SUMMARY

Various embodiments of infusion systems and related apparatus, and methods of operating the same are described. One or more, or all of certain embodiments described herein may be employed using a computer or similar system. In some embodiments, a test article fluid solution in one or more syringes is delivered by pump in alternating intervals with the maintenance fluid solution in one or more syringes. In some embodiments, the intervals are the same duration. In other embodiments, the intervals may vary. In some embodiments, at least two separate test article solutions are delivered by pump in a manner whereby maintenance solution is delivered immediately prior to and following delivery of each of the at least two test article solutions.

In some embodiments, a test article fluid delivery rate is programmed by an operator into a computer and/or pump for use when the test article is calculated to be in the syringe or the tubing set. A maintenance fluid delivery rate is programmed by an operator into the computer or pump for use when no test article is calculated to be in the pump syringe or in the tubing set.

In some embodiments, test article and/or maintenance fluid delivery rates are programmed into the computer or pump and do not change for the duration of the infusion study. In some embodiments, test article and/or maintenance fluid delivery rates are updated at defined time intervals to reflect changes in animal weight.

In some embodiments, delivery of a maintenance fluid solution in one or more syringes is followed by an essentially non-stop delivery of test article fluid solution in one or more syringes.

In some embodiments, a plurality of pumps is communicatively coupled with a network comprising at least one computer.

In some embodiments, a computer is programmed by an operator to maintain a schedule for the at least two pumps to be loaded with test article fluid syringes and maintenance fluid syringes.

In some embodiments, each of the at least two pumps will notify the operator of loading of an incorrect fluid syringe according to the programmed schedule.

In some embodiments, the operator inputs into a computer or into the at least two pumps a single dead volume value to apply to the at least two like tubing sets connected to the at least two pumps such that all tubing sets have the same dead volume value. In some embodiments, the operator inputs into a computer or into the at least two pumps a dead volume value for each of the at least two like tubing sets such that it is possible that one tubing set has a different dead volume value than another tubing set. In certain embodiments, one tubing set is coupled to one pump such that the fluid path of a syringe loaded in a pump and the fluid path of the tubing set are communicatively coupled.

In some embodiments, the computer, or the at least two pumps, calculate in substantially real-time which fluid solution is entering (from the end of the tubing set not connected to a syringe) the animal's bloodstream. These calculations are according to calculated leading and trailing edges of the test article fluid solution and the leading and trailing edges of the maintenance fluid solution. The leading and trailing edges can be calculated based on pump or computer knowledge, at each point in time, of which fluid solution syringe is loaded in a pump, the pump fluid delivery rate, and tubing set dead volume.

In some embodiments, the pump or computer may vary a pump delivery rate to affect the test article's leading edge entry into the bloodstream coinciding with an operator-selected time. This time may be a time for the operator to collect a blood (or other) sample or observe an animal. In some embodiments, the pump or system may calculate and notify the operator of the time of the test article's leading edge entry into the bloodstream. This time may be, for example, a time for the operator to collect a blood (or other) sample or observe an animal.

In some embodiments, a memory device may be in data communication with each pump and the computer. One memory device may be communicatively coupled with one pump. The memory device may receive data from the computer and deliver this data to a pump upon receipt, or at a later time. The memory device or memory devices may temporarily or permanently record data from the pump.

In some embodiments, at least two pumps operate independently or a pump may not operate as part of a network. Each pump may be individually communicatively coupled with an individual computer.

BRIEF DESCRIPTION OF THE DRAWINGS

Advantages of the present invention will become apparent to those skilled in the art with the benefit of the following detailed description and upon reference to the accompanying drawings in which:

FIG. 7 is a chart that illustrates an exemplary infusion schedule in accordance with one or more embodiments of the present technique.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF ILLUSTRATIVE EMBODIMENTS

As used herein, the term "syringe" refers to a small device consisting of a glass, metal, or polymeric tube, narrowed at its outlet, and fitted with either a piston or a rubber bulb for drawing in a quantity of fluid or for ejecting fluid in a stream, for cleaning wounds, injecting fluids into the body, etc.

As discussed in more detail below, certain embodiments of the present technique include a system and method for controlled infusion of substances to a test subject.

In toxicology infusion studies involving many animals, new chemical entities or other compounds to be tested (often termed "test articles") may be delivered in fluid form by pumps to animals intravenously or via other routes of administration. The fluid form may be delivered either continuously or intermittently over periods lasting, for example, one or more weeks. As used herein, fluid form may include liquids, gases, or solids.

A test article solution interval may include one or more test article solution syringes. In certain embodiments of an infusion method, the test article fluid solution is loaded into syringes (or other fluid containing vessels, such as plastic bags), which are loaded in syringe pumps or similar style pumps. Typically, the syringe connects to a tubing set. The open end of the tubing set not connected to the syringe may be inserted in an animal's blood vein or other blood vessels, organs, or spaces, thereby communicating fluid solution in the syringe with the animal's bloodstream and/or other parts or systems. Other routes of administration of test article and maintenance fluid solutions besides venous may include arterial, intestinal, peritoneal, cerebrospinal fluid spaces (e.g., spinal, ventricular, etc), and other body organs and spaces. Additionally, "maintenance" (also termed "flush") fluid solutions (e.g., saline or lactated Ringers solution) may be delivered to maintain positive fluid flow prior to a start of a continuous infusion or during intermittent infusion intervals when test article is not being delivered or to separate different test articles. A maintenance solution interval may comprise one or more maintenance solution syringes. As described in more detail below, an infusion study protocol may require delivery of two or more test article fluid solutions with each test article being infused in discrete intervals.

Continuous infusion may involve delivering to an animal a test article in an essentially non-stop manner over the course of an extended period, such as one or more weeks. The rate of test article delivery may be a constant rate or may be updated periodically to increase the delivery rate proportionately to a change in animal body weight. Continuous infusion requires the user to repeatedly reload syringes containing test article until each animal receives the targeted cumulative test article volume required by the infusion study protocol. An interval of maintenance fluid delivery may precede the test article delivery.

Intermittent infusion may involve delivering a test article over a fixed amount of time, such as one hour, at essentially the same time over numerous periods, such as over multiple 24 hour periods. For example, pumps may deliver intermittently as follows: one hour of test article followed by approximately 23 hours of maintenance fluid followed by one hour of test article followed by approximately 23 hours of maintenance fluid and so on until each animal receives the targeted cumulative test article volume required by the infusion study protocol. If test article is in the tubing set when it is loaded into the pump, the maintenance fluid may first displace (or "purge") the test article remaining in the tubing set resulting in the delivery of the test article into the animal's bloodstream. The maintenance fluid interval (e.g., 23 hours) may be approximate in order that the operator is not required to commence a test article fluid interval at precisely the same time (e.g., at the exact same time each day).

After the maintenance fluid delivery displaces all test article from the tubing set, the maintenance fluid serves to maintain fluid flow into the animal such that the open end of a tubing set dwelling in an animal's vein does not occlude, such as may be caused by clotted blood. Such occlusion may hinder the delivery of test article solutions thereby delaying or prohibiting successful delivery of the targeted cumulative test article volume required by the infusion study protocol. It may be further noted that the test article fluids delivered over numerous test article fluid infusion intervals may need to be delivered according to certain infusion study-defined time constraints.

In the case of an intermittent infusion study in animals, a user may document the time of loading and unloading of syringes and the time of starting and stopping of pumps. Additionally, the user may calculate and document during each intermittent interval the time at which the test article's leading edge of fluid enters the animal's bloodstream (e.g., the time at which test article begins entering the animal's bloodstream) and the time at which the test article's trailing edge enters the animal's bloodstream (e.g., the time at which test article no longer is being delivered into the animal's bloodstream). The test article's trailing edge is typically adjacent or at least substantially adjacent to the maintenance fluid's leading edge and the maintenance fluid's trailing edge is at least substantially adjacent to the test article's leading edge.

For example, a syringe containing maintenance fluid solution may be loaded into the pump. Maintenance fluid solution may be the only fluid in the syringe and tubing set. After a period of maintenance fluid delivery, the operator may "switch" syringes by disconnecting the tubing set from the maintenance fluid syringe and removing the maintenance fluid syringe from the pump. The operator may then connect the tubing set, which still contains maintenance fluid, to a syringe filled with test article fluid and load into the pump the test article fluid syringe. Before the pump begins delivering the contents of the test article syringe, the fluid path leading into the animal includes the tubing set filled with maintenance fluid and the test article syringe filled with test article fluid. After the pump begins delivering the contents of the test article syringe, the test article fluid will begin displacing (purging) the maintenance fluid in the tubing set, thus pushing maintenance fluid into the animal's bloodstream.

The operator may know the exact or approximate fluid volume of the tubing set. This volume value is termed the "dead volume." This dead volume value (e.g., in mL) together with the pump fluid delivery rate or rates (e.g., in mL/hour) at which the pump is set to operate, allow the operator to calculate the time required for the test article fluid in a syringe newly loaded into a pump to displace (purge) the maintenance fluid dead volume from the tubing set. Similarly, this dead volume value (e.g., in mL) together with the pump delivery rate or rates (e.g., in mL/hour) at which the pump is set to operate, allow the operator to calculate the time required for the maintenance fluid in a syringe newly loaded into a pump to displace (purge) the test article fluid dead volume from the tubing set. As the toxicology infusion studies are undertaken to measure the test article effects on each animal, operators desire to know at which point in time each animal is receiving (e.g., in its bloodstream) test article and at what delivery rate. The user may desire to know all test article delivery start and stop times and test article volumes delivered. Thus, the operator may have to calculate the location in the tubing set of the leading and trailing edges of the test article fluid and the maintenance fluid.

Study protocols for such intermittent infusions may require one rate of test article delivery and a separate rate of maintenance fluid delivery. These rates may be fixed according to gender, animal weight, dosing level grouping, or the like. These rates may be periodically adjusted based on each animal's weight.

Based on techniques described herein, operators may perform tasks, for example, collect blood samples at operator defined time points following the entry of the test article's leading edge into the animal's bloodstream. This blood sampling may be used to study the pharmacokinetics of the test article's distribution in the animal's circulatory system. Other operator tasks required at operator defined time points may include general animal health observation, neurologic animal health observations, removal of animal access to drinking water, etc.

Figure 1:
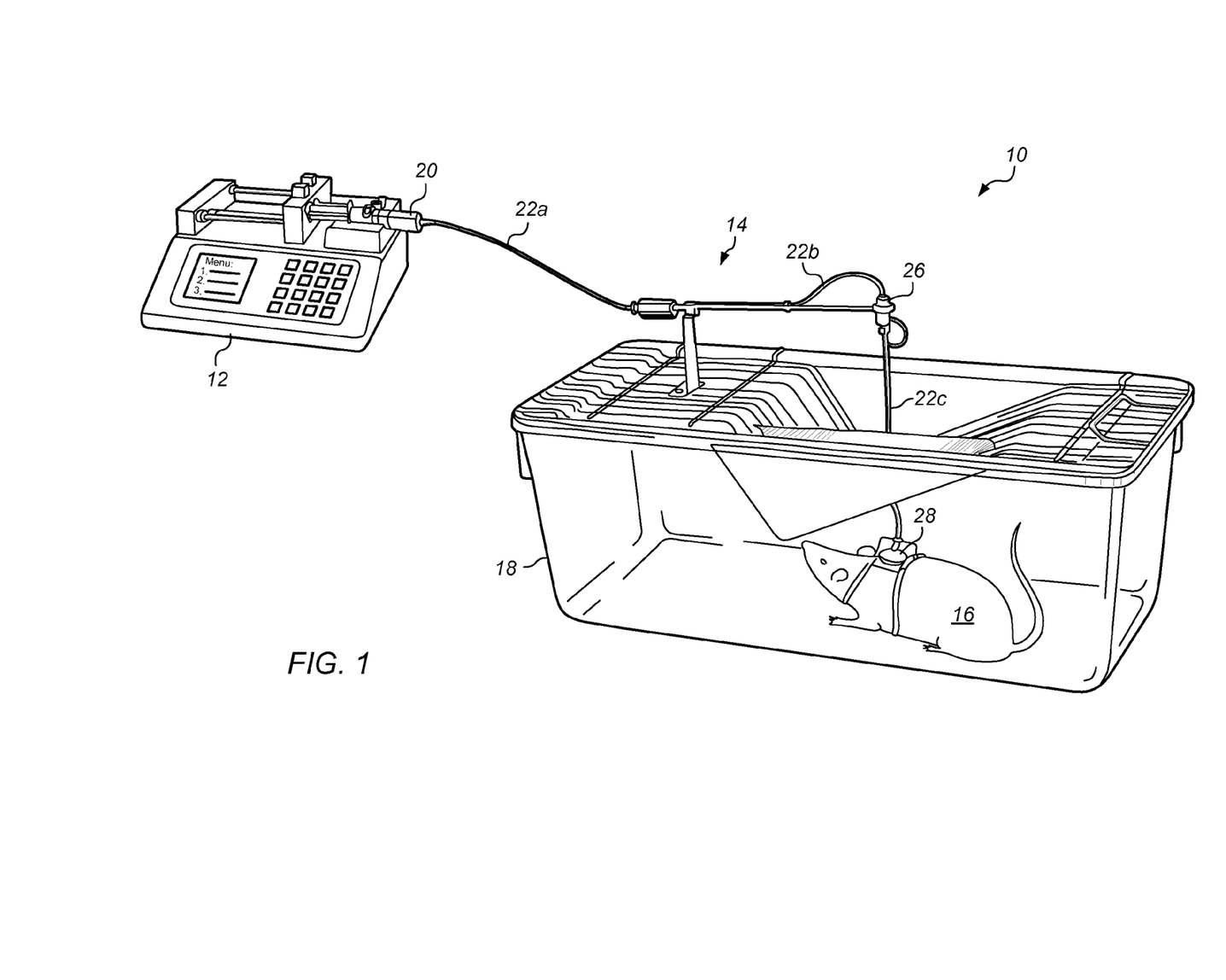
FIG. 1 is a diagram that illustrates a fluid delivery system in accordance with one or more embodiments of the present technique.

Turning now to the figures, FIG. 1 illustrates a fluid delivery system 10, in accordance with one or more embodiments of the present technique. In certain embodiments, fluid delivery system 10 includes one or more devices used to infuse a test subject with a test substance. In the illustrated embodiment, fluid delivery system 10 includes pump 12, tubing set 14, test subject 16 (e.g., a rat) and enclosure 18. During use, a substance may be delivered in a controlled manner from pump 12 to test subject 16 in enclosure 18 via tubing set 14.

Figure 2:
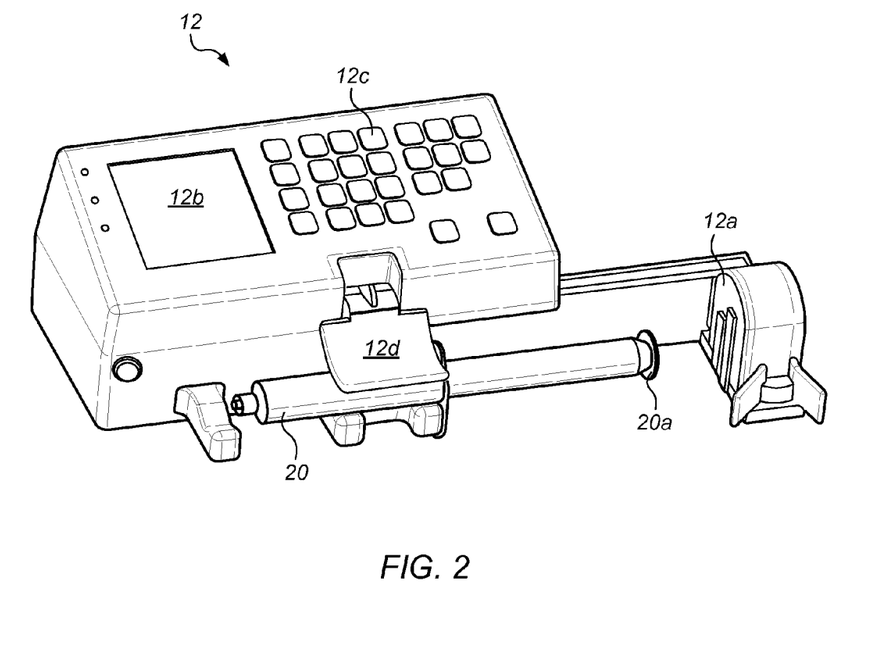
FIG. 2 is a diagram that illustrates a pump and a syringe in accordance with one or more embodiments of the present technique.

An embodiment of pump 12 is depicted in FIG. 2. Pump 12 may include a displacement device that pressurizes and/or advances a fluid (e.g., a liquid, gas or solid) into test subject 16. For example, in the illustrated embodiment, pump 12 includes ram 12a that engages plunger 20a of syringe 20 during use. Pump 12 may also include a user interface. For example, in the illustrated embodiment, pump 12 includes graphical display 12b (e.g., an LCD screen) and inputs 12c (e.g., a keypad).

In certain embodiments, pump 12 is capable of assessing and/or determining a type, size, or other characteristics associated with syringe 20. For example, in the embodiment of pump 12 and syringe 20 depicted in FIG. 2, pump 12 includes syringe assessment device 12d capable of assessing/detecting a size/type of syringe 20. In some embodiments, syringe assessment device 12d is capable of measuring and determining a size (e.g., an outer diameter) of a barrel of syringe 20. In certain embodiments, an operator selects a syringe manufacturer, brand, type, or the like from a library of syringe manufacturers, brands, or types that is stored in a memory (e.g., memory of pump 12 and/or memory of an associated computer device). In certain embodiments, pump 12 operates using parameters (e.g., stored parameters) for accurate fluid delivery that are based on the operator selection and/or the assessed/detected syringe type/size.

In certain embodiments, pump 12 assesses outer diameter of syringe 20 and uses the outer diameter in combination with the type of syringe (assessed or input by the user) to determine the inner diameter of the syringe. Pump 12 may then operate using the determined inner diameter to accurately deliver fluid to the test subject.

In certain embodiments, pump 12 includes one or more infusion type pumps. For example, pump 12 may include one or more of an electromechanical infusion pump such as, but not limited to, a syringe pump, a piston pump, a peristaltic pump, a diaphragm pump, a large volume pump, a stationary ("pole mount") pump, and a portable ("ambulatory") type pump. In some embodiments, one or more pumps are coupled to a single test subject.

In certain embodiments, pump 12 includes a single channel syringe pump. A single channel syringe pump may include an infuse/withdraw rack capable of handling a single syringe. In some embodiments, pump 12 includes a multi-channel syringe pump. A multi-channel syringe pump may include an infuse/withdraw rack capable of handling two or more syringes simultaneously. As shown in FIG. 1, single tubing set 14 is coupled between single pump 12 and single test subject 16. Other embodiments may include a plurality of pumps coupled to a single test subject or a single pump coupled to multiple test subjects.

Pump 12 may be operated manually or automatically. For example, an operator may program and monitor each pump 12 manually and/or operation of pump 12 may be automated such that little to no user/operator interaction is required. In certain embodiments, pump 12 is controlled (e.g., operated and monitored) via a control system, such as a computer. In some embodiments, more than one pump 12 may be provided in fluid delivery system 10. The pumps 12 may be operated in coordination to provide test substances to one or more test subjects 16 in a controlled manner. For example, the infusion rates of fluid from one or more pumps 12 may be regulated such that a certain sequence of fluid infusion into one or more test subjects 16 is provided.

In certain embodiments, pump 12 may include a pressure sensor in communication with the fluid path of tubing set 14 and syringe 20, or a force sensor in communication with plunger 20a of syringe 20. When a defined value for pressure or force is exceeded and/or sensed by pump 12, an alarm and/or notification may activate pump 12 and/or a computer device/system in communication with pump 12. Such an alarm and/or notification may be termed an "occlusion alarm." In some embodiments, pump 12 stops delivering fluid until the force or pressure condition activating the occlusion alarm is resolved.

In certain embodiments, fluid delivery system 10 and/or pump 12 are integrated with a computer or computer system described herein. For example, the fluid delivery system or pump may have an integrated computer that performs the functions of the computer or computer system described herein. In some embodiments, fluid delivery system 10 and/or pump 12 operates independently (e.g., they do not operate as part of a network of a computer system and one or more other fluid delivery systems and/or pumps).

In certain embodiments, fluid delivery system 10 (e.g., a pump 12) delivers a gas or gases to test subject 16. In some embodiments, fluid delivery system 10 delivers a liquid or liquids to test subject 16. In other embodiments, fluid delivery system 10 delivers a solid or solids to test subject 16. In some embodiments, fluid delivery system 10 delivers a combination of liquid, gas, or solid to an animal.

In certain embodiments, a fluid delivery system or pump delivers (advances) an infusion fluid in accordance with an "infusion routine". Infusion routines may involve one or more parameters in selected combinations. Examples of infusion routine parameters include, but are not limited to: at least one rate (e.g., mL/hour), at least one volume (e.g., mL), at least one time (e.g., start, end), and at least one duration (e.g., hour).

In certain embodiments, combinations of infusion routine parameters are limited to allowable combinations of infusion routine parameters. Thus, a certain infusion routine parameter may not be combined with one or more other infusion routine parameters or with selected combinations of infusion routine parameters. Allowable combinations of infusion routine parameters may be determined, for example, by the type of infusion fluid, type of fluid delivery system, type of pump, and other factors involved with the infusion of the test subject with the infusion fluid. Examples of allowable combinations of infusion routine parameters include, but are not limited to, at least one rate with at least one volume (e.g., mL); at least one rate with either at least one duration (e.g., hour) or at least one time (e.g., start, end); at least one volume with either at least one duration or at least one time (e.g., start, end). Allowable combinations of infusion routine parameters may vary, however, based on the desired use of the infusion routine (e.g., the experimental method being used with the infusion fluid). The range of allowable combinations of infusion routine parameters may, for example, be expanded with further study of the interaction of infusion routine parameters.

As depicted in FIG. 1, tubing set 14 may include a conduit used to direct an infusion fluid from pump 12 into test subject 16. In certain embodiments, tubing set 14 includes various combinations of catheters, polymeric tubing, fluid swivels, luer connectors, metal tubing for connecting, air filters, particle filters, and the like. In the illustrated embodiment, tubing set 14 includes conduit 22a (coupled to syringe 20), conduit 22b, fluid swivel 26, conduit 22c, and catheter 28 coupled to test subject 16. Other embodiments may include a variety and combination of devices capable of delivering an infusion fluid to test subject 16.

Figure 3:
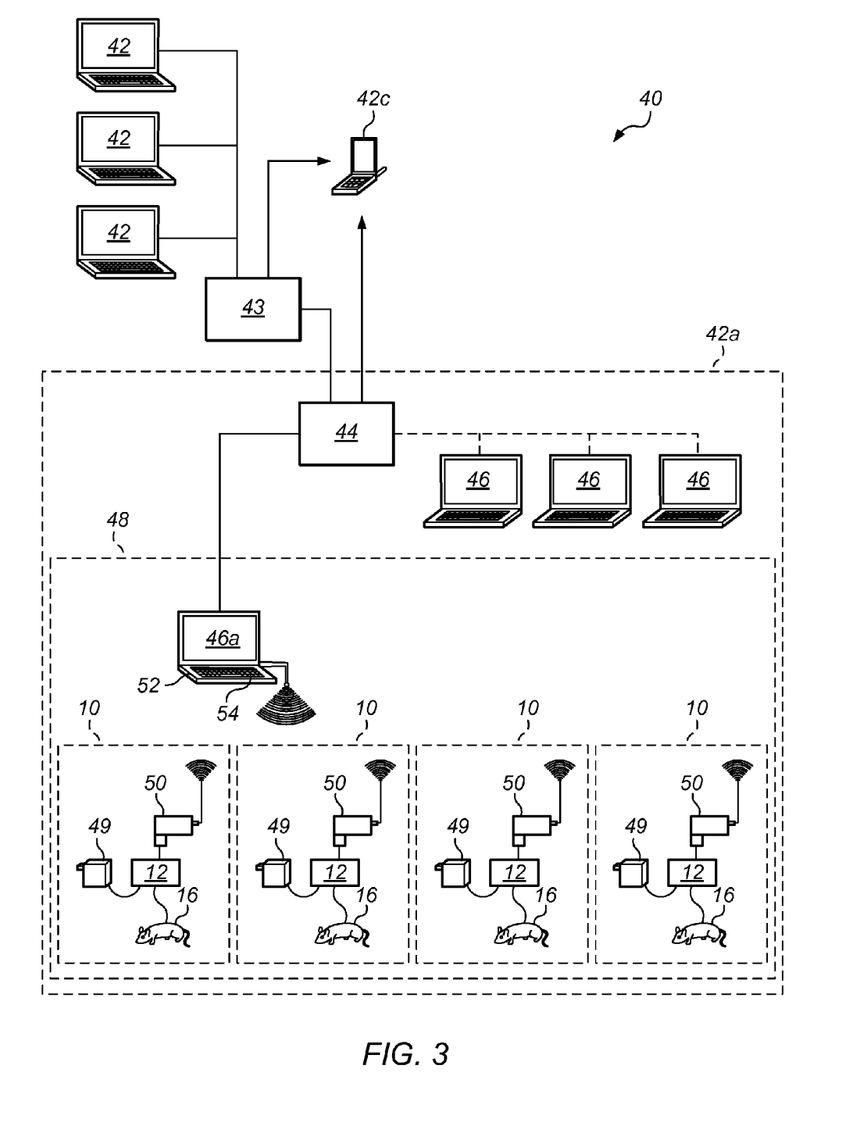
FIG. 3 is a schematic diagram of a fluid infusion network in accordance with one or more embodiments of the present technique.

In some embodiments, one or more fluid delivery systems 10 are provided in a network. FIG. 3 is a diagram that illustrates fluid infusion network 40 ("network 40"). Network 40 may include one or more fluid delivery systems 10 that are capable of being connected to and/or networked with other fluid delivery systems 10. In the illustrated embodiment, network 40 includes a plurality of remote users 42 and facility 42a interconnected via internet 43 or a similar network of devices. Each of the devices coupled to internet 43 may be in communication with one another via the internet or via another communication method. For example, in the illustrated embodiment, server 44 of facility 42a is in direct communication with remote device 42c (e.g., a mobile computer/cellular device).

In the illustrated embodiment, facility 42a includes server 44 in communication with a plurality of computer devices 46 also coupled to internet 43. Server 44 may be hard wired or wirelessly connected to computer devices 46. In the illustrated embodiment, one of computer devices 46 includes fluid infusion system host device 46a of fluid infusion system 48 in communication with a plurality of fluid delivery systems 10. Each of delivery systems 10 includes pump 12 coupled to test subject 16. Pump 12 and other portions of fluid delivery system 10 are coupled to and/or powered by power supply 49. A common or independent power supply 49 may be provided for each of fluid delivery systems 10 and/or other devices of network 40. Fluid delivery systems 10 may be in communication with host device 46a and/or other devices on network 40. In the illustrated embodiment, each of fluid delivery systems 10 includes communication device 50 in communication with host device 46a. In an embodiment, communication device 50 includes a wired or wireless network device (such as a wireless network card and/or an Ethernet port).

In certain embodiments, fluid infusion network 40 includes one or more devices capable of executing an infusion routine that can be used to operatively control, monitor, receive, and/or store data from one or more devices of fluid infusion network 40. For example, one or more computer devices of remote users 42, such as computer devices 46, host device 46a, communication device 50, and/or one or more components of fluid delivery system 10 (e.g., pump 12) may include a processor that implements one or more routines, such as infusion methods or routines, and/or receiving and storing data from pumps. In some embodiments, one or more computer devices of remote users 42, such as computer devices 46 and/or host device 46a, include a computer readable medium having program instructions stored thereon that are used to implement one or more methods in accordance with one or more embodiments of the present technique. For example, in the illustrated embodiment, host device 46a includes memory 52 having program instructions/routines stored thereon and processor 54 capable of executing the program instructions/routines.

In certain embodiments, host device 46a is capable of communicating with one or more of fluid delivery systems 10. For example, in the illustrated embodiment, host device 46a is communicatively coupled with at least two of fluid delivery systems 10. Accordingly, host device 46a may be communicatively or at least operatively coupled to pump 12 of delivery system 10.

Embodiments may include any variety of infusion techniques and associated monitoring and control. During use, an infusion network (e.g., infusion network 40 and/or fluid delivery system 10) may be employed to infuse a test subject (e.g., test subject 16) with a fluid.

Figure 6:
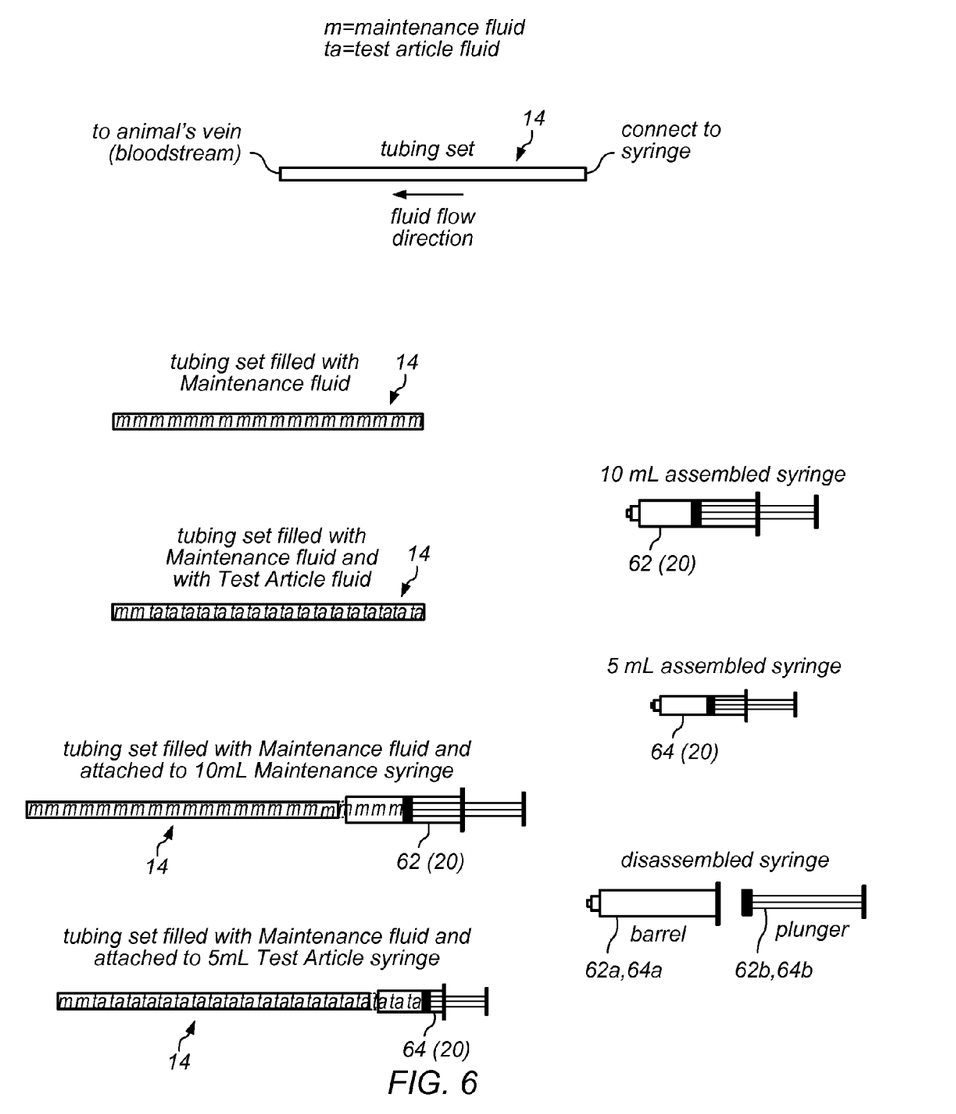
FIG. 6 is a diagram that illustrates various syringe types in accordance with one or more embodiments of the present technique.

During use of system 10, an operator may select and assign a syringe size/type from one or more sizes/types stored in memory 52 of host device 46a or pump 12. In certain embodiments, the size/type of syringe 20 to be used to assess the syringe and/or implement delivery characteristics are unique to only a test article fluid solution or only a maintenance fluid solution. In certain embodiments, the syringe type or size for a test article delivery is not the same as the syringe size/type for a maintenance delivery. FIG. 6 illustrates various syringe size/types. In the illustrated embodiment, maintenance syringe 62 and test article syringe 64 are depicted with each having different sizes. Each of maintenance syringe 62 and test article syringe 64 may include barrel 62a, 64a and plunger 62a, 64b, respectively. FIG. 6 also depicts tubing set 14 being filled with maintenance fluid (m) and/or test article fluid (ta) at various points during infusion.

Use of different types of syringes 20 for each solution in combination with syringe assessment device 12d may enable host device 46a and/or pump 12 to differentiate between test article fluid syringes 64 and maintenance syringes 62 that are loaded in pump 12. This differentiation enables the following: (a) automatic flow rate assessment/determination/assignment by pump 12 (e.g., one flow rate for test article syringes 64 and another flow rate for maintenance syringes 62); (b) documentation of a type of fluid solution syringe loaded into pump 12; (c) notification to operator of which syringe or solution type to load into pump 12 (e.g., on display 12b (e.g., via an audible tone, LED indicator light of pump 12, on display 12b (e.g., LCD screen) of pump 12, on a graphical display of a computer of host device 46a or other computer devices 42, 42c, 46, via email or SMS text message to a computer device, such as device 42c, etc.); and/or (d) notification to operator if the pump(s) and/or computer system detect the wrong syringe type loaded into pump 12 and/or instruction of correct syringe type to load (e.g., via an audible tone, LED indicator light of pump 12, on display 12b (e.g., LCD screen) of pump 10, on a graphical display of a computer of host device 46a or other computer devices 42, 42c, 46, via email or SMS text message to a computer device, such as device 42c, etc.).

Figure 8:
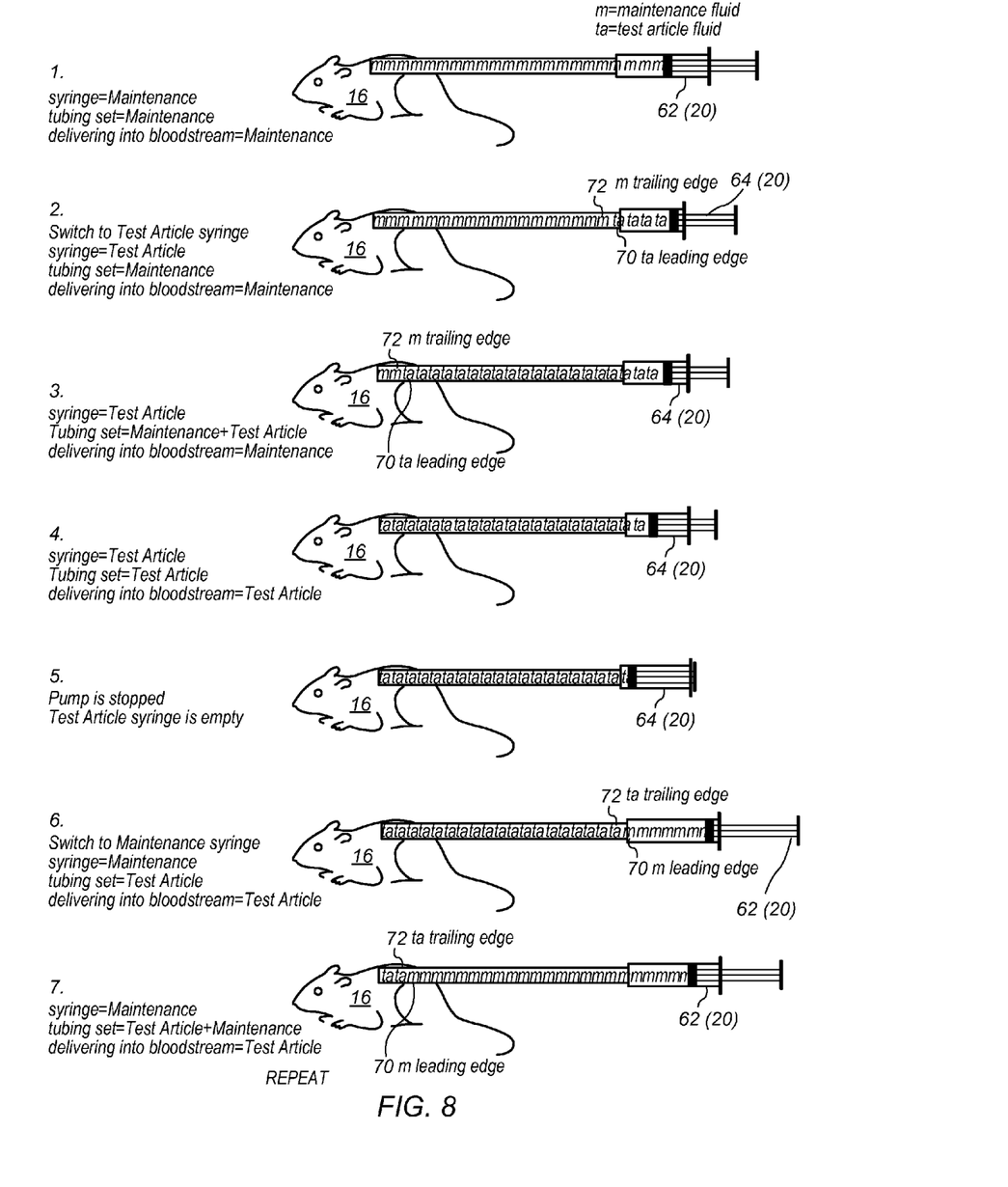
FIG. 8 depicts various illustrations of leading and trailing edges in accordance with one or more embodiments of the present technique.

In some embodiments, a network of at least two pumps is in data communication with a computer system. In one such embodiment, the user inputs a single value for the tubing set dead volume common to at least two fluid delivery systems 10 and/or pumps 12. In some embodiments, a user and/or a computer system (e.g., host system 46a) calculates the location of leading edge 70 and trailing edge 72 (shown in FIG. 8) of each fluid type in the fluid set (e.g., in the syringe loaded in the pump, in the tubing set, or entering the animal's bloodstream from the end of the tubing set not connected to the syringe). FIG. 8 depicts illustrations of leading edges 70 and trailing edges 72 at various times during a repeatable cycle for infusion of test subject 16 with maintenance fluid (m) and test article fluid (ta) from maintenance syringe 62 and test article syringe 64, respectively.

The type of fluid (e.g., either test article or maintenance fluid) in syringe 20 being delivered by pump 12 may be known by syringe size data obtained automatically via use of syringe assessment device 12d and/or a manual input. For instance, in another embodiment, the operator, when loading syringe 20 into pump 12, may provide an input/indication (e.g., enter via pushing a button on keypad 12c, shown in FIG. 2) that test article fluid syringe 64 and/or a maintenance fluid syringe 62 is being loaded in pump 12. For instance, a user may provide an input (e.g., a manual input) indicative of the substance type (e.g., test article or maintenance substance) contained in a syringe. In some embodiments, pump 12 includes a device in data communication with pump 12 and host device 46a and/or other devices (such as computer devices 42, 42c and 46), such as a device capable of reading/assess/detecting a unique identifying feature (e.g., bar code, RFID chip, printed number, etc.) of syringe 20 being loaded.

In certain embodiments, a user inputs into a computer system (e.g., host device 46a and/or pump 12) test article delivery rates and/or maintenance fluid delivery rates which may or may not be unique to each of at least two pumps 12. In some embodiments, a user inputs parameters directing that when test article is in a syringe loaded in the pump or when test article is in the tubing set, the pump will deliver fluids at the test article delivery rate. In such embodiments, the associated computer system documents the time and type of each syringe during loading and unloading. In some embodiments, during each interval in an intermittent infusion study, an associated computer system calculates and records the time at which the test article's leading edge commences entry into the test subject's bloodstream and the time at which the test article's trailing edge commences entry into the test subject's bloodstream. In some embodiments, the associated computer system documents the time when each pump stops delivery and the time when each pump starts delivery. In this manner, the computer system is operable to document the respective times, delivery rates, interval volumes, and cumulative volumes of test article fluid delivery and/or the respective times, delivery rates, interval volumes, and cumulative volumes of maintenance fluid delivery to each test subject.

In certain embodiments, the trailing and leading edges of test article and/or maintenance fluid solutions are calculated based on when they commence entry into an animal's catheter, the most distal (e.g., distal from the pump) component of a tubing set. In such embodiments, the trailing and leading edges of test article and/or maintenance fluid solutions may not be calculated based on when they commence entry into the animal's bloodstream.

In certain embodiments, dead volume is provided via various methods. In some embodiments, dead volume inputs can be provided manually or via a computer one pump at a time, to all pumps in a network and/or one pump at a time. In some embodiments, a computer is operable to receive (from user or other external source, e.g., another computer) and distribute a single dead volume value to one or multiple pumps. For instance, in a network of three-hundred pumps, the user can input one dead volume value that covers all pumps. This single dead volume value may enable a computer and/or pump to automatically make necessary flow calculations.

Figure 4:
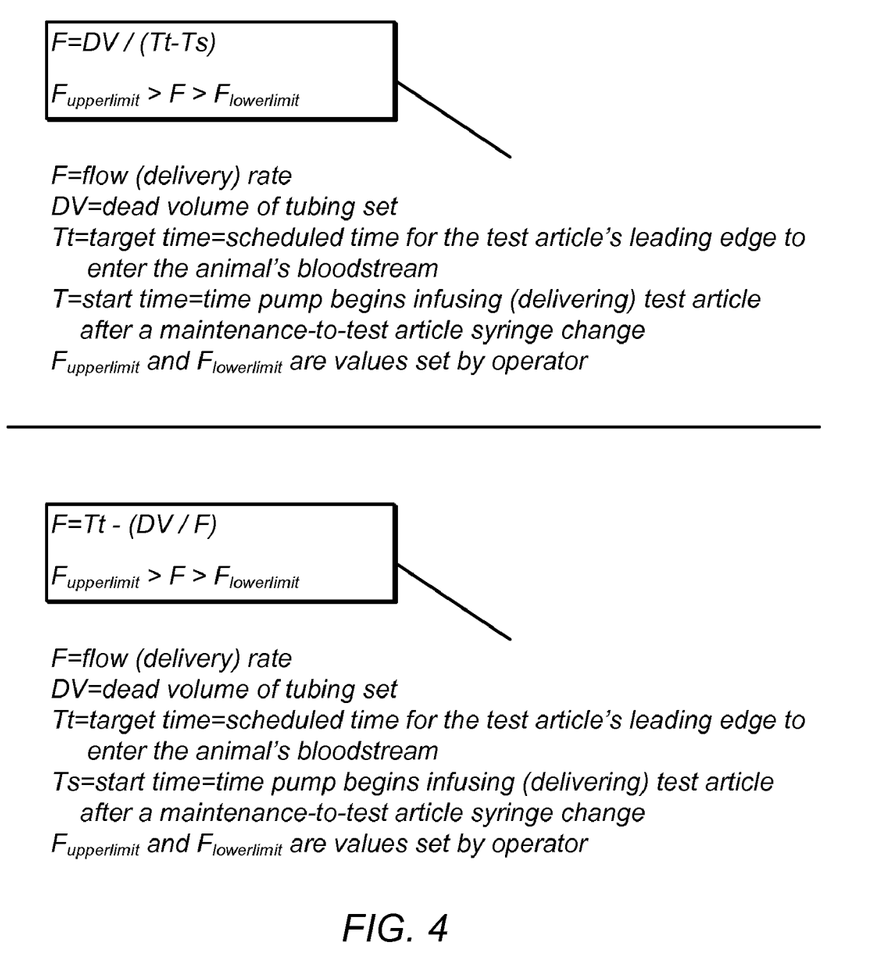
FIG. 4 illustrates various parameters in accordance with one or more embodiments of the present technique.

In certain embodiments, a computer system and/or pump changes a pump delivery rate to result in a test article fluid solution's leading edge commencing entry into the animal's bloodstream at an operator selected time point. In some embodiments, the computer or pump begins syringe fluid delivery based on pump delivery rate. In one such embodiment, the time at which the test article's leading edge commences entry into the animal's bloodstream coincides with a time point defined by the operator. In some embodiments, change of a pump delivery rate is subject to an operator defined upper limit delivery rate and an operator defined lower limit delivery rate. In an embodiment, a computer or pump notifies the operator that the operator defined time point may not be valid due to these delivery rate constraints. FIG. 4 illustrates relationships between various flow rates (e.g., upper and lower limits), dead volumes, target times and start times.

In some embodiments, a pump and/or computer provides a display indicative of a substance exiting a conduit and being delivered to the test subject. For example, in an embodiment a pump/computer identifies/displays, at any point in time, which substance is exiting conduit (or tubing set) and entering animal's blood vessel, organ or space.

Figure 5A:
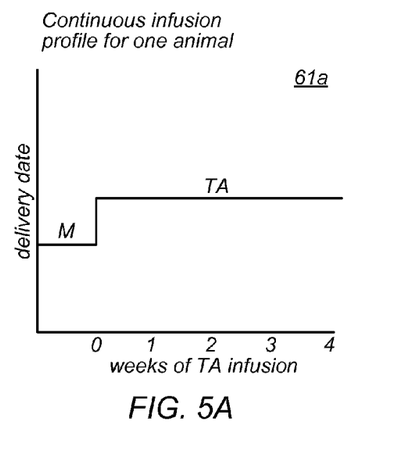
FIGS. 5A-5D are plots that depict timing/volumes of infusion in accordance with one or more embodiments of the present technique.
Figure 5B:
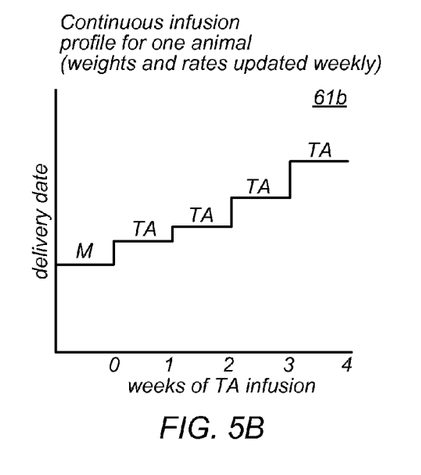
Figure 5C:
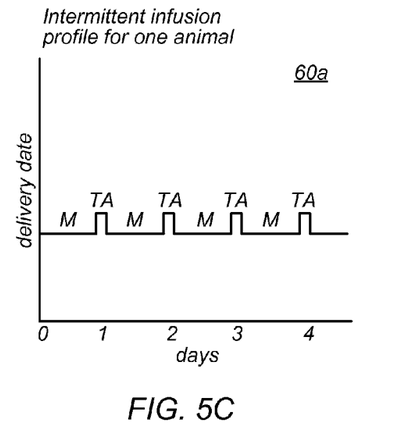
Figure 5D:
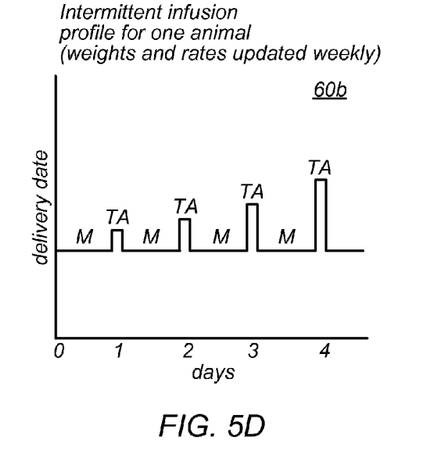

FIGS. 5A-5D depict plots of the timing of infusion in accordance with one or more embodiments of the present technique. FIGS. 5C and 5D illustrate intermittent infusion profiles for an animal in accordance with one or more embodiments of the present technique. Repeated cycles of alternating test article and maintenance solution infusion ("intermittent infusion") are represented by plots 60a and 60b. In some embodiments, at least two pumps, each having a syringe assessment device, are programmed by an operator for intermittent infusion. In certain embodiments, the test article solution and maintenance solution are delivered in an alternating manner, as depicted in FIGS. 5C and 5D. For example, test article (TA) may be infused into test subject 16 for two hours during every 24-hour period for 30 days. The two-hour test article infusion may occur at approximately the same time each day. Therefore, two hours of test article solution infusion (TA) would occur over two hours on day one, followed by approximately 22 hours of maintenance fluid solution infusion (M), followed by two hours of test article solution infusion (TA) on day two, followed by approximately 22 hours of maintenance fluid solution infusion (M), and so on for a total of 30 days. In some embodiments, a test article daily target volume value is used in lieu of test article infusion duration. For example, a given amount of an article may be injected as opposed to an injection based only on the duration of the injection. In some embodiments, start and stop times of injection are used in lieu of, or in combination with, test article infusion duration. In some embodiments, these parameters (e.g., test article infusion duration, start/stop times, and daily target volume value) are applied as a series of parameters.

FIGS. 5A and 5B illustrate continuous infusion profiles for an animal in accordance with one or more embodiments of the present technique. In certain embodiments, an interval of maintenance fluid solution infusion is followed by one or more intervals of test article fluid solution infusion ("continuous infusion") as represented by plots 61a and 61b. Such a continuous infusion may comprise a maintenance fluid solution infusion interval lasting one or several days and utilizing one or more syringes filled with maintenance fluid solution. The maintenance solution interval (M) may serve to condition animals to an infusion study apparatus (e.g., system 10) and the associated environment. A test article fluid solution infusion interval (TA) which may last one day, several days, or several weeks may follow the maintenance solution interval. The infusion study may reach its end point upon the conclusion of the test article solution interval.

Based on the above described embodiments of the present technique, a plurality of pumps and a computer system may be communicatively coupled with at least two of the plurality of pumps. Each pump may include a mechanism for detecting a syringe barrel's outer diameter. In some embodiments, a test article fluid solution is assigned (e.g., via computer or pump) to one syringe type (e.g., size and manufacturer), and a maintenance fluid solution is assigned (e.g., via computer and/or pump 12) to a syringe type different from the test article syringe type assigned. In some embodiments, differentiation between test article syringes and maintenance syringes may be affected using bar codes on syringes and bar code readers attached to or in data communication with pumps. In some embodiments, differentiation between test article syringes and maintenance syringes may be affected by using RFID chips on syringes and RFID chip readers attached to or in data communication with pumps.

FIG. 7 is a chart that illustrates an exemplary infusion schedule in accordance with one or more embodiments of the present technique.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Furthermore, note that the word "may" is used throughout this application in a permissive sense (i.e., having the potential to, being able to), not a mandatory sense (i.e., must). The term "include", and derivations thereof, mean "including, but not limited to". As used in this specification, the singular forms "a", "an" and "the" include plural referents unless the content clearly indicates otherwise. Thus, for example, reference to "a syringe" includes a combination of two or more syringes. The term "coupled" means "directly or indirectly connected".

What is claimed is:

1. A fluid infusion system, comprising:
   one or more fluid infusion pumps;
   a conduit configured to provide a path for delivery of one or more infusion fluids from an infusion fluid reservoir to an animal test subject; and
   a computer configured to assess, based at least in part on a flow computation for at least one of the infusion fluids, a location of a trailing edge and/or a leading edge of one or more of the infusion fluids as a first infusion fluid and a second infusion fluid are advanced in succession through the conduit toward the animal test subject, wherein the trailing edge and/or the leading edge comprises an interface between the first infusion fluid and the second infusion fluid;
   wherein the computer is configured to assess the location of the trailing edge and/or the leading edge of one or more of the infusion fluids at one or more points in time and to store in a memory of the computer the location of the trailing edge and/or the leading edge at the one or more points in time.

2. The fluid infusion system of claim 1, wherein the conduit comprises a tubing set.

3. The fluid infusion system of claim 1, wherein the infusion fluid reservoir comprises a syringe.

4. The fluid infusion system of claim 1, wherein the first infusion fluid comprises a test article substance and the second infusion fluid comprises a maintenance substance.

5. The fluid infusion system of claim 1, further comprising a first infusion fluid reservoir configured to contain the first infusion fluid, and a second fluid infusion reservoir configured to contain the second infusion fluid, wherein the second infusion fluid is different from the first infusion fluid.

6. The fluid infusion system of claim 1, wherein the computer is configured to assess the location of the trailing edge and/or the leading edge of one or more of the infusion fluids based at least in part on a volume of fluid that has been advanced into the conduit from the infusion fluid reservoir.

7. The fluid infusion system of claim 1, wherein the computer is configured to notify a user and/or stop advancement of an infusion fluid when the leading edge and/or the trailing edge is at or near an outlet of a tubing set of the conduit.

8. The fluid infusion system of claim 1, wherein the computer is configured to assess a dead volume of one or more of the infusion fluids within the conduit and/or the infusion fluid reservoir.

9. The fluid infusion system of claim 8, wherein the dead volume comprises the dead volume of fluid located within a tubing set of the conduit.

10. The fluid infusion system of claim 8, wherein the computer is configured to assess an input indicative of the dead volume to assess the dead volume of one or more of the infusion fluids.

11. The fluid infusion system of claim 10, wherein the input is a user input.

12. The fluid infusion system of claim 8, wherein the computer is configured to assess the location of the trailing edge and/or the leading edge based on at least in part on a value of the dead volume of infusion fluid located upstream and/or downstream of the leading edge and/or the trailing edge.

13. The fluid infusion system of claim 8, wherein the fluid infusion pump is configured to advance an infusion fluid through the conduit by advancing a sufficient amount of the infusion fluid to displace the dead volume of fluid located within the conduit.

14. The fluid infusion system of claim 1, wherein the path for the delivery of the infusion fluid comprises the infusion fluid exiting an outlet of a tubing set and entering a blood vessel, organ, or other space of the test subject.

15. The fluid infusion system of claim 1, wherein the computer is configured to assess at what point a portion of an infusion fluid should be located within the conduit based on the volume of one or more of the infusion fluids advanced into the conduit to assess the location of the trailing edge and/or the leading edge of one or more of the infusion fluids.

16. A method of infusing a fluid into a test subject, comprising:
   advancing, using a fluid pump system, one or more infusion fluids to an animal test subject via a conduit;
   assessing, using the fluid pump system, based at least in part on a flow computation computation for at least one of the infusion fluids, a location of a trailing edge and/or a leading edge of one or more of the infusion fluids as a first infusion fluid and a second infusion fluid are advanced in succession through the conduit toward the animal test subject, wherein the trailing edge and/or the leading edge comprises an interface between the first infusion fluid and the second infusion fluid; and
   notifying a user and/or stopping advancement of an infusion fluid when the leading edge and/or the trailing edge is at or near an outlet of a tubing set of the conduit to provide an output indicative of the location of the trailing edge and/or the leading edge of one or more of the infusion fluids.

17. The method of claim 16, further comprising providing an output indicative of the location of the trailing edge and/or the leading edge of one or more of the infusion fluids as the infusion fluids are advanced through the conduit.

18. The method of claim 16, further comprising assessing a location of the trailing edge and/or the leading edge of one or more of the infusion fluids in an infusion fluid reservoir and a tubing set to assess the location of the trailing edge and/or the leading edge of one or more of the infusion fluids.

19. The method of claim 16, further comprising assessing at what point a portion of an infusion fluid should be located within the conduit based on the volume of one or more of the fluid infusion fluids advanced into the conduit to assess the location of the trailing edge and/or the leading edge of one or more of the infusion fluids.

20. The method of claim 16, comprising:
   automatically varying, using a fluid infusion pump, the delivery rate and/or a start time of advancement of an infusion fluid such that the leading edge of a test article solution begins entry into a blood vessel, organ, or space of a test subject at an operator defined time point.

21. The fluid infusion system of claim 1, wherein the computer is configured to assess the location of the trailing edge and/or the leading edge based at least in part on a dead volume value of the conduit and a fluid delivery rate of the fluid infusion pump.

22. The fluid infusion system of claim 1, further comprising a network of at least two of the fluid infusion pumps communicatively coupled to the computer, wherein the computer is configured to assess the location of the trailing edge and/or the leading edge based at least in part on a dead volume value provided by a user and a fluid delivery rate of the fluid infusion pump.

23. The fluid infusion system of claim 1, further comprising a network of at least two of the fluid infusion pumps communicatively coupled to the computer, wherein the computer is configured to assess, based on a single dead volume value provided by a user, the location of the trailing edge and/or the leading edge as infusion fluids are advanced by each of at least two of the fluid infusion pumps in the network.

24. The fluid infusion system of claim 1, further comprising:
a network of at least two of the fluid infusion pumps communicatively coupled to the computer; and
two or more conduits, wherein each of at least two of the conduits is configured to carry infusion fluids to a different animal test subject,
wherein the computer is configured to assess, for each of the at least two of the conduits, the location of an interface between a first infusion fluid and a second infusion fluid as the first fluid and the second fluid are advanced in the conduit toward an animal test subject.

25. A fluid infusion system, comprising:
one or more fluid infusion pumps;
a conduit configured to provide a path for delivery of one or more infusion fluids from an infusion fluid reservoir to an animal test subject; and
a computer configured to assess, based at least in part on a flow computation for at least one of the infusion fluids, a location of a trailing edge and/or a leading edge of one or more of the infusion fluids as a first infusion fluid and a second infusion fluid are advanced in succession through the conduit toward the animal test subject, wherein the trailing edge and/or the leading edge comprises an interface between the first infusion fluid and the second infusion fluid;
wherein the computer is configured to notify a user and/or stop advancement of an infusion fluid when the leading edge and/or the trailing edge is at or near an outlet of a tubing set of the conduit.

26. A fluid infusion system, comprising:
one or more fluid infusion pumps;
a conduit configured to provide a path for delivery of one or more infusion fluids from an infusion fluid reservoir to an animal test subject;
a computer configured to assess, based at least in part on a flow computation for at least one of the infusion fluids, a location of a trailing edge and/or a leading edge of one or more of the infusion fluids as a first infusion fluid and a second infusion fluid are advanced in succession through the conduit toward the animal test subject, wherein the trailing edge and/or the leading edge comprises an interface between the first infusion fluid and the second infusion fluid; and
a network of at least two of the fluid infusion pumps communicatively coupled to the computer, wherein the computer is configured to assess, based on a single dead volume value provided by a user, the location of the trailing edge and/or the leading edge as infusion fluids are advanced by each of at least two of the fluid infusion pumps in the network.

* * * * *